(12) United States Patent
Graumann

(10) Patent No.: US 8,744,150 B2
(45) Date of Patent: Jun. 3, 2014

(54) METHOD FOR DETERMINING A LAYER ORIENTATION FOR A 2D LAYER IMAGE

(75) Inventor: Rainer Graumann, Höchstadt (DE)

(73) Assignee: Siemens Aktiengesellschaft, Munich (DE)

(*) Notice: Subject to any disclaimer, the term of this patent is extended or adjusted under 35 U.S.C. 154(b) by 216 days.

(21) Appl. No.: 13/450,701

(22) Filed: Apr. 19, 2012

(65) Prior Publication Data

US 2012/0269411 A1    Oct. 25, 2012

(30) Foreign Application Priority Data

Apr. 19, 2011    (DE) .......................... 10 2011 007 667

(51) Int. Cl.
*G06K 9/00*    (2006.01)

(52) U.S. Cl.
USPC .......................................... 382/128

(58) Field of Classification Search
USPC .......................................... 382/128; 600/140
See application file for complete search history.

(56) References Cited

U.S. PATENT DOCUMENTS

| | | | |
|---|---|---|---|
| 2007/0223800 A1* | 9/2007 | Guehring | 382/131 |
| 2008/0317204 A1* | 12/2008 | Sumanaweera et al. | 378/65 |
| 2010/0082365 A1* | 4/2010 | Noordvyk et al. | 705/2 |

FOREIGN PATENT DOCUMENTS

DE    102006012945 A1    10/2007

* cited by examiner

*Primary Examiner* — Gregory F Cunningham
(74) *Attorney, Agent, or Firm* — Laurence A. Greenberg; Werner H. Stemer; Ralph E. Locher

(57) ABSTRACT

A layer orientation is determined for a 2D layer image that is to be generated from 3D image data of an anatomical object in the body of a patient. First, a model resembling the object that is imaged in the 3D image data is selected from a model pool. The model has an assigned default orientation in a permanently selected relative position with respect to the model. While the relative position is being maintained, the model is aligned with the 3D image data so as to match the model to the object with maximum coincidence. The default orientation established relative to the 3D image data is then selected as the layer orientation for the 3D image data.

5 Claims, 2 Drawing Sheets

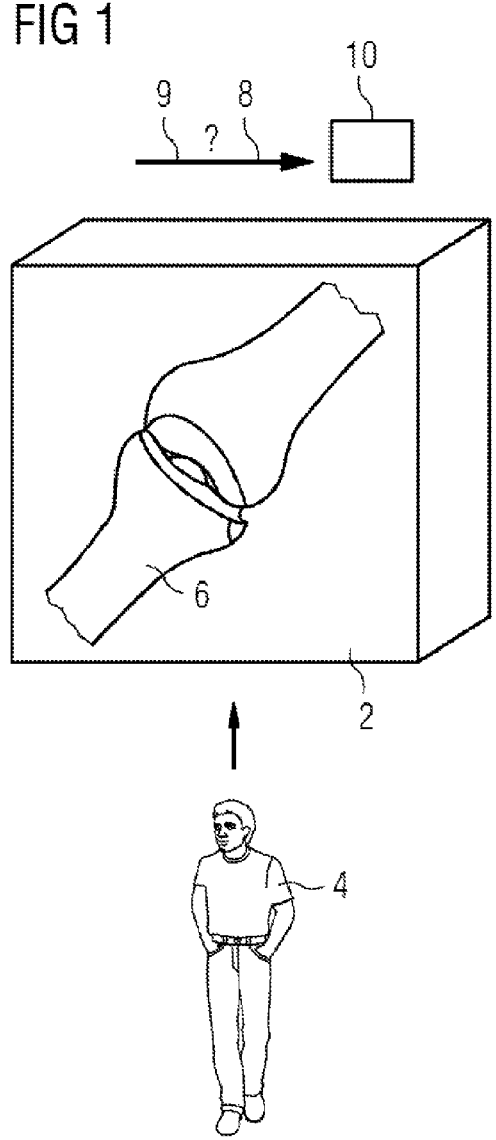
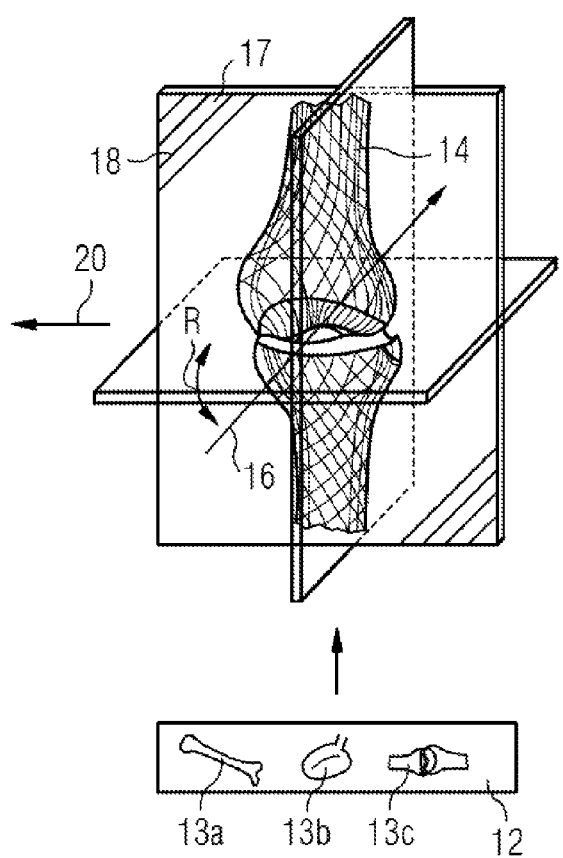
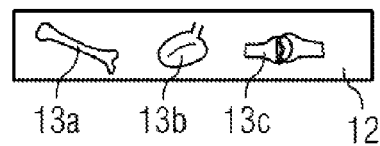

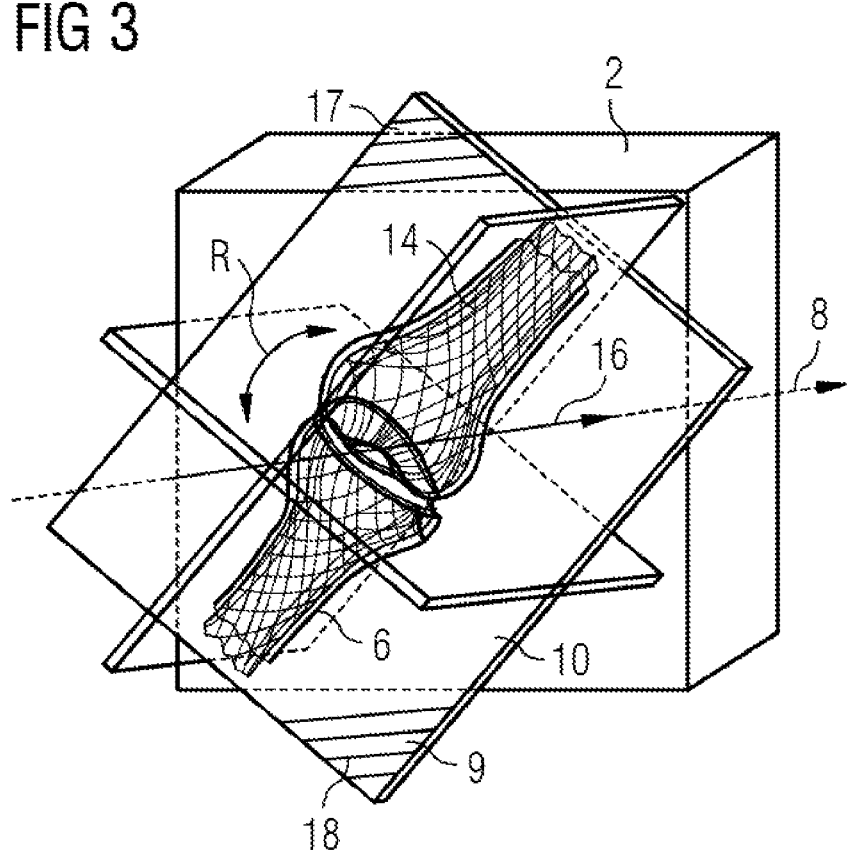

METHOD FOR DETERMINING A LAYER ORIENTATION FOR A 2D LAYER IMAGE

CROSS-REFERENCE TO RELATED APPLICATION

This application claims the priority, under 35 U.S.C. §119, of German patent application DE 10 2011 007 667.0, filed Apr. 19, 2011; the prior application is herewith incorporated by reference in its entirety.

BACKGROUND OF THE INVENTION

Field of the Invention:

The invention relates to a method for determining a layer orientation for a 2D layer image that is to be generated from 3D image data of an anatomical object in a patient's body.

Patients' 3D image data or, as the case may be, 3D data records is/are increasingly being generated in the field of medical imaging for 3-dimensionally imaging a respective anatomical object in the patient's body. Examples of such anatomical objects include organs, bones, and joints in the patient's body. 3D image data is usually visualized in the form of 2D layer images. Multiplanar reformatting (MPR) is an instance of what is known. Layers of a 3D data record are here displayed as 2D layer images, with the layer orientation being defined—at least in the case of planar layers or locally—by a projection direction perpendicular to the layer. There is established, as a rule, the layer, which is also to take a curved course, for example. For simplicity's sake, reference is here repeatedly made to the projection direction, although the invention can be applied also to selecting the position of layers having any shape.

For representing 3D image data using MPR there are defined standards which, depending on the specific organ in the patient's body or his/her ailment or, as the case may be, on the object being imaged, establish the respective layer orientation requiring to be shown as the default orientation (and hence the projection direction) for 2D layer images obtained from the 3D image data. That applies in particular to bone imaging when the anatomical object is accordingly a bone or, as the case may be, joint in the patient's body. The default orientation's position relative to the (standardized) object is thereby established for all layer representations of any patients.

In certain radiological applications, computed tomography for instance, the required or, as the case may be, correct layer orientation is produced automatically in the image data: That is possible because the patient always lies in a defined position in the recording device when the 3D image data is being recorded. The image data or, as the case may be, the object being imaged therefore has a defined spatial position or, as the case may be, orientation in a given coordinate system of the 3D image data.

Intraoperative applications for generating 3D image data such as, for instance, 3D C-arc imaging are, though, also known. The initial situation is different here as there is broad scope for freely selecting the patient's respective position relative to the imaging system. Thus the anatomical object's position or, as the case may be, orientation in the 3D image data is not predefined or, as the case may be, is not comparable or standardized for different recordings.

For 3D image data of such kind it is hence first necessary to determine an appropriate layer orientation or, as the case may be, imaging direction, for example an optimal layer orientation or, as the case may be, default orientation or one specified according to medical standards for certain joints.

It is known that the surgeon or surgical assistant first has to process the intraoperatively recorded 3D image data manually, which is to say as a rule has to turn and move it to determine and present the optimal or, as the case may be, standardized layer orientation or position. That takes extra operating time with possible changing between a sterile and non-sterile area, and it also requires experienced personnel. In other words the layer orientation for the 2D layer images is here established by hand based on a subjective consideration and assessment of the 3D image data.

SUMMARY OF THE INVENTION

It is accordingly an object of the invention to provide a process for determining the layer orientation of a two-dimensional layer image which overcome the above-mentioned disadvantages of the heretofore-known devices and methods of this general type and which provides for an improved method for determining a layer orientation for the above-cited case.

With the foregoing and other objects in view there is provided, in accordance with the invention, a method for determining a layer orientation for a 2D layer image to be generated from 3D image data of an anatomical object in a body of a patient. The method comprises:

selecting from a model pool a model resembling the anatomical object imaged in the 3D image data, the model having been assigned a default orientation in a permanently selected relative position with respect to the model;

while maintaining the relative position, aligning the model with the 3D image data in order to match the model to the object with maximum coincidence; and selecting the default orientation established relative to the 3D image data as the layer orientation for the 3D image data.

In other words, the objects of the invention are achieved by way of the novel method as claimed. A real anatomical object in a patient's body has already been imaged or, as the case may be, actually been recorded from the patient in the 3D image data. When the 3D image data has been generated, a (virtual) model of the object as closely as possible resembling the object imaged in the 3D image data is first selected from a model pool. The relevant model has already been preassigned a default orientation standardized for said model, for example, or one that is optimal or only desired. The default orientation is assigned to the model in a permanently selected relative position. So in other words the relevant default orientation has been established in advance for the model; the default orientation will be turned or moved compliantly when the model is turned or moved so that the same relative position will always be maintained. With the position relative to the default orientation being maintained, the model will then be aligned with the 3D image data. Aligning takes place such that the model will have been matched to the object with maximum coincidence. Thus what is termed a "best-fit" process is carried out. In other words the model will be "fitted" to the actual image of the anatomical object in the 3D image data by moving, rotating, or scaling. It is also conceivable to fit only a part ("partial fitting") of the—for instance statistical—model to the object, thus to the bone if, say, a part of a joint is broken.

Finally the default orientation established through moving or rotating the model relative to the—real, imaged—object and hence to the 3D image data is selected as the layer orientation for the 3D image data, so for actually generating the layer image from the object.

The method according to the invention can be fully automated by means of image-processing algorithms. The method offers the advantage that layer orienting or, as the case may be, selecting that corresponds to default orienting is performed for any 3D image data. The default (layer) orientations are established on the model in a fixed relative position, are adjusted compliantly during the fitting process, and finally accepted for the real data. The result is hence an ensuing representation of the 3D image data in correspondingly desired or optimal directions.

Determining a layer orientation in a complex manner using the imaged object is replaced by simpler matching of the model to the object followed by automatically establishing the layer orientation. So a complex and possibly error-prone user intervention is no longer required for selecting the layer orientation.

Valuable theater time can be saved and sources of errors reduced. Thus, for example, layer selecting and representing MPR layers can be performed fully automatically.

The inventive method can be used also for methods, such as computed tomography cited above, having per se standardized or, as the case may be, reproducible layer orienting. Here, too, applying the method will make it possible to eliminate, for example, a patient's imprecise or even incorrect positioning in the interests of optimal or, as the case may be, correct layer orienting. The consequent advantage lies in no longer having to be so concerned about the patient's being in a particularly rigidly defined position during a relevant CT recording session. The patient can be positioned in virtually any way, which will in turn enhance his/her comfort.

The inventive step is primarily found in that there is employed an object model, for example a bone model, on which standard or, say, default layer orientations have been established once in a complex procedure, and in that there is employed the usually easy-to-perform and less error-prone process of fitting the model to the actually imaged anatomical object.

In a preferred embodiment variant of the method the model pool contains at least one model for each of the types of anatomical objects in a patient's body that are of interest. There will then, for example, be a model in the model pool for each human bone and joint and each human organ customarily requiring to be examined. It should be noted here that while the method can indeed be generally applied also to non-rigid objects, for example a patient's liver, the accuracy that can be achieved will be limited in such cases owing to the object's motion. Hence a system executing the method will need only to be informed of the specific object imaged in the 3D image data to be able to select the corresponding correct model. That can be done for example interactively by the surgeon performing imaging or by an assistant. The selection can, though, also be made automatically through an image comparison, for example.

In another preferred embodiment variant of the invention the object is hence a bone structure in the patient's body with the model then being a corresponding model of the bone structure. Bone structures, so bones and joints, are as a rule the main target of a corresponding imaging operation.

The aforementioned method is particularly advantageous especially for bones and also joints because the layer orientations, which is to say projection directions, accordingly requiring to be selected need to have been selected with particular care here so that, for example, reliable diagnoses can be made about, say, the patient's joint functionality.

In another preferred embodiment variant the model is a statistically averaged model of the same object in different patients' bodies. In other words, for producing, for example, a model of a knee joint a multiplicity of different patients' knee joints are statistically averaged in order to produce a standardized averaged knee model. The probability that a corresponding knee model can be matched particularly well to the actually imaged anatomical object will then be particularly high. Models can, though, alternatively also be used as images of typical patients, for example healthy patients or patients with typical diagnoses.

It is alternatively conceivable to use an object of an as a rule healthy side of the patient as a mirror-image model for the object of the patient's other, for example injured side. That only requires for there to be an image of the healthy side obtained, for example, from a pre-operative whole-body CT scan.

In another preferred embodiment variant of the method the default orientation assigned to the model is a clinically standardized default orientation for the same objects in different patients' bodies. Standardized layer orientations for assessing 3D image data offer the advantage that comparable diagnoses for different patients can here be made by different doctors. When standardized default layer orientations of such kind are anchored to the model, the method will finally also supply standardized layer orientations for generating the 2D layer images.

Alongside clinically standardized default orientations it is, though, possible also to establish on the model what are termed "optimal" default orientations—or, as the case may be, viewing directions—which, depending on the specific clinical issue, can also differ for the same objects, for instance. For example, different viewing directions are optimal for a diagnosis made on a hip joint depending on whether a worn or a broken hip joint is to be diagnosed on a part of a hip joint. Those are two different clinical issues and so require different viewing directions and hence different default orientations. Depending on the doctor's selection, by choosing corresponding (identical) models having different default orientations it will then be possible to automatically switch between different viewing directions for the same object in a patient's body.

Other features which are considered as characteristic for the invention are set forth in the appended claims.

Although the invention is illustrated and described herein as embodied in a method for determining a layer orientation for a 2D layer image, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 1 is a schematic sketch of a patient's 3D image data in which an anatomical object is imaged;

FIG. 2 is a schematic sketch of a model that corresponds to the anatomical object and has established default orientations; and FIG. 3 is a schematic sketch of the 3D image data having determined layer orientations.

DETAILED DESCRIPTION OF THE INVENTION

Referring now to the figures of the drawing in detail and first, particularly, to FIG. 1 thereof, there is shown 3D image data 2 that has been recorded from a patient 4, in this case from their knee joint. An object 6, namely the knee joint, of the patient 4 is thus imaged in the 3D image data 2. The aim is to determine the relative position of a layer orientation 9 or, as the case may be, projection direction 8 (only indicated in FIG. 1 by an arrow) for 3D image data 2. The determined position will then serve to generate a 2D layer image 10 from 3D image data 2. According to the invention, there is provided a model pool 12: It contains in each case one model for each type of object 13*a*, 13*b*, 13*c* generally found in patients' bodies. Type 13*a* is therein a femur, type 13*b* a dorsal vertebra, and type 13*c* a knee joint.

According to FIG. 2, a model 14 of object 6 similar to object 6, so a type 13*c* knee-joint object, is selected from a model pool 12. An imaging direction 16 or, as the case may be, a default orientation 17 perpendicular thereto (in the form of an imaging plane 18, indicated in FIG. 2 by hatching) has already been pre-established on model 14 or, as the case may be, for each type 13*a*-*c* by way of a complex procedure. Default orientation 17 (or, as the case may be, imaging direction 16) corresponds here to one of the planes or, as the case may be, layers conforming to the MPR clinical standard that are shown in FIG. 2 for representing knee joints. Default orientation 17 occupies a fixed relative position R with respect to model 14, indicated in FIG. 2 by an arrow.

Arrow 20 indicates that model 14 is now oriented on 3D image data 2 or, as the case may be, object 6. That is done in such a way that model 14 will fit as coincidently as possible onto object 6. Fitting is done by, for example, iteratively turning, moving, and scaling model 14 relative to object 6 in a process performed automatically by an image-processing system.

FIG. 3 shows the result on completion of optimal matching, meaning with as close as possible a fit. During the matching process, imaging direction 16 or, as the case may be, default orientation 17 remains in an unchanged relative position R with respect to model 14. So in other words, default orientation 17 or, as the case may be, the position of imaging plane 18 is scaled, moved, or rotated together with model 14 relative 3D image data 2 or, as the case may be, object 6.

Default orientation 17 is finally selected as layer orientation 9 for 3D image data 2 so that the final result, indicated by imaging plane 18, is a 2D projection image 10, in this case a sectional or, as the case may be, layer representation through the knee joint of patient 4.

In other words, the position of layer orientation 9 relative to 3D image data 2 is therefore not the result of its being determined directly with reference to object 6 but indirectly by way of matching model 14 to object 6 and using default orientation 17 established in advance on model 14.

The following is a list of reference numberals and symbols used in the above description.

- 2 3D image data
- 4 Patient
- 6 Object
- 8 Projection direction
- 9 Layer orientation
- 10 2D layer image
- 12 Model pool
- 13*a* Type
- 13*b* Type
- 13*c* Type
- 14 Model
- 16 Imaging direction
- 17 Default orientation
- 18 Imaging plane
- 20 Arrow
- R Relative position

The invention claimed is:

1. A method for determining a layer orientation for a 2D layer image to be generated from 3D image data of an anatomical object in a body of a patient, wherein the method comprises:
   selecting from a model pool a model resembling the anatomical object imaged in the 3D image data, the model having been assigned a default orientation in a permanently selected relative position with respect to the model;
   while maintaining the relative position, aligning the model with the 3D image data in order to match the model to the object with maximum coincidence; and
   selecting the default orientation established relative to the 3D image data as the layer orientation for the 3D image data.

2. The method according to claim 1, wherein the model pool contains at least one model for each of a plurality of types of anatomical objects.

3. The method according to claim 1, wherein the object is a bone structure in the body of the patient.

4. The method according to claim 1, wherein the model is a statistically averaged model of a given object in bodies of a plurality of different patients.

5. The method according to claim 1, wherein the default orientation assigned to the model is a clinically standardized default orientation for the same objects in bodies of a plurality of different patients.

* * * * *